United States Patent
Manusu

[19]
[11] Patent Number: 5,954,934
[45] Date of Patent: Sep. 21, 1999

[54] CASSETTE FOR ELECTROPHORETIC GELS

[75] Inventor: Howard Pericles Manusu, Hunters Hill, Australia

[73] Assignee: Gradipore Limited, North Ryde, Australia

[21] Appl. No.: 09/000,117
[22] PCT Filed: Jul. 12, 1996
[86] PCT No.: PCT/AU96/00441
§ 371 Date: Mar. 18, 1998
§ 102(e) Date: Mar. 18, 1998
[87] PCT Pub. No.: WO97/04307
PCT Pub. Date: Feb. 6, 1997

[30] Foreign Application Priority Data

Jul. 14, 1995 [AU] Australia .................... PN 4190

[51] Int. Cl.$^6$ .................................................. G01N 27/26
[52] U.S. Cl. .................................................... 204/618
[58] Field of Search .................... 204/456, 465, 204/467, 606, 615, 616, 618, 619, 620

[56] References Cited

U.S. PATENT DOCUMENTS 5,288,465 2/1994 Margolis .................. 422/102

FOREIGN PATENT DOCUMENTS

WO 95/31717 11/1995 WIPO.

OTHER PUBLICATIONS

Proceedings, Annual Technical Conference Proceedings—Society of Vacuum Coaters 1992, Published by Society of Vacuum Coaters, Albuquerque NM, USA, p. 431.

*Primary Examiner*—Robert Warden
*Assistant Examiner*—Alex Naguerola
*Attorney, Agent, or Firm*—Michael J. Striker

[57] ABSTRACT

A cassette (10) for use in the formation of an electrophoretic gel comprising two plates with substantially planar walls (11, 13) each having two sides and two ends so arranged in a side-by-side, spaced apart array to form a gel receiving space (15) between them, the improvement consisting of a plurality of projections (16) on one or each of the plates, the projections extending into the gel receiving space and the projections being so sized and so spaced apart over the surface of one or each of the plates that when a gel is introduced into the gel receiving space and a well-forming comb is inserted into the space, a plurality of spaced wells are formed in the gel, at least some of the wells being separated by a tongue of gel which surrounds and engages at least one of the projections, wherein the projections prevent the tongues of the gel from moving relative to the two plates when the electrophoretic gel is in use.

14 Claims, 3 Drawing Sheets

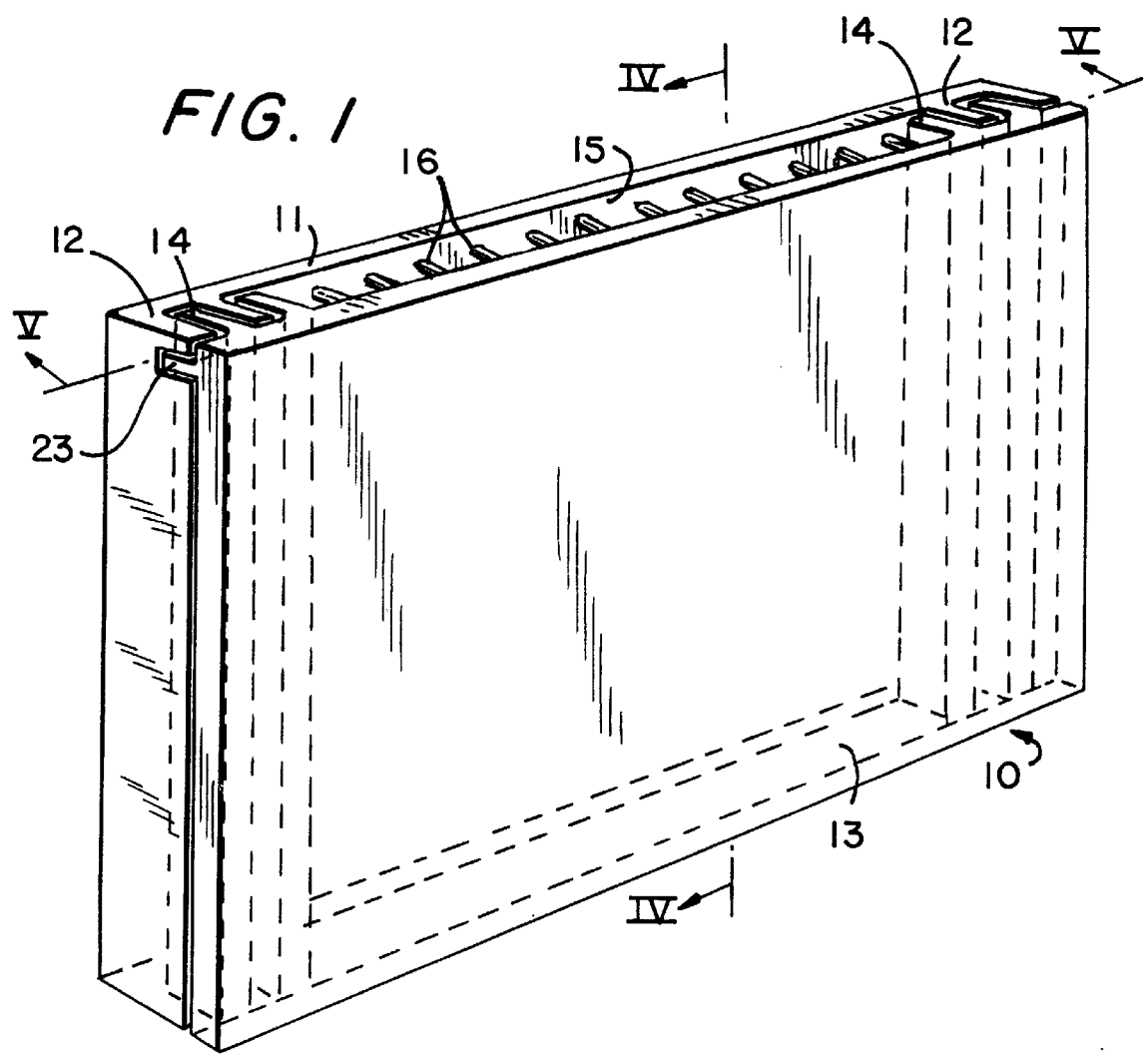
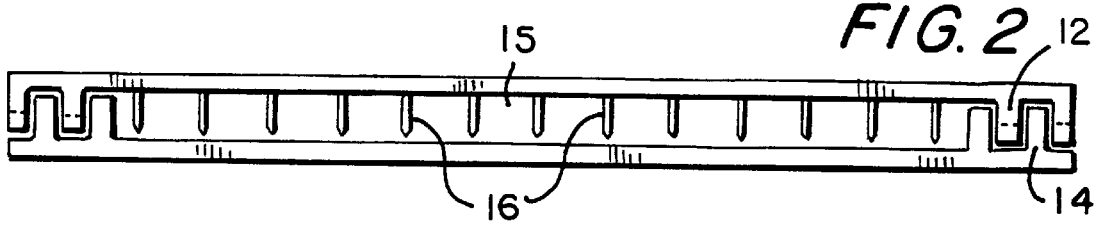
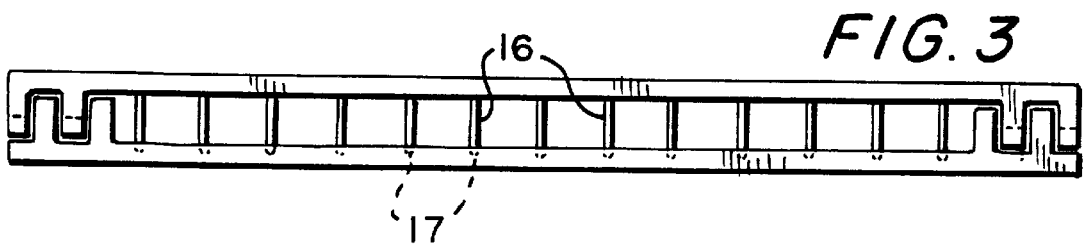

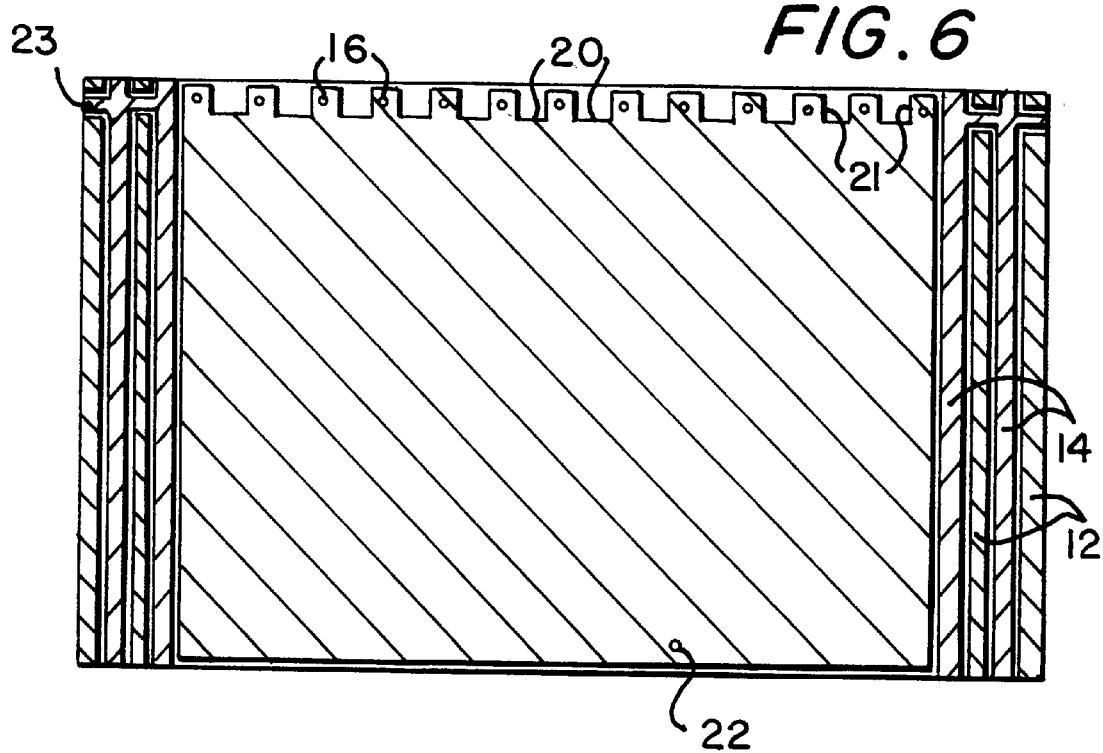
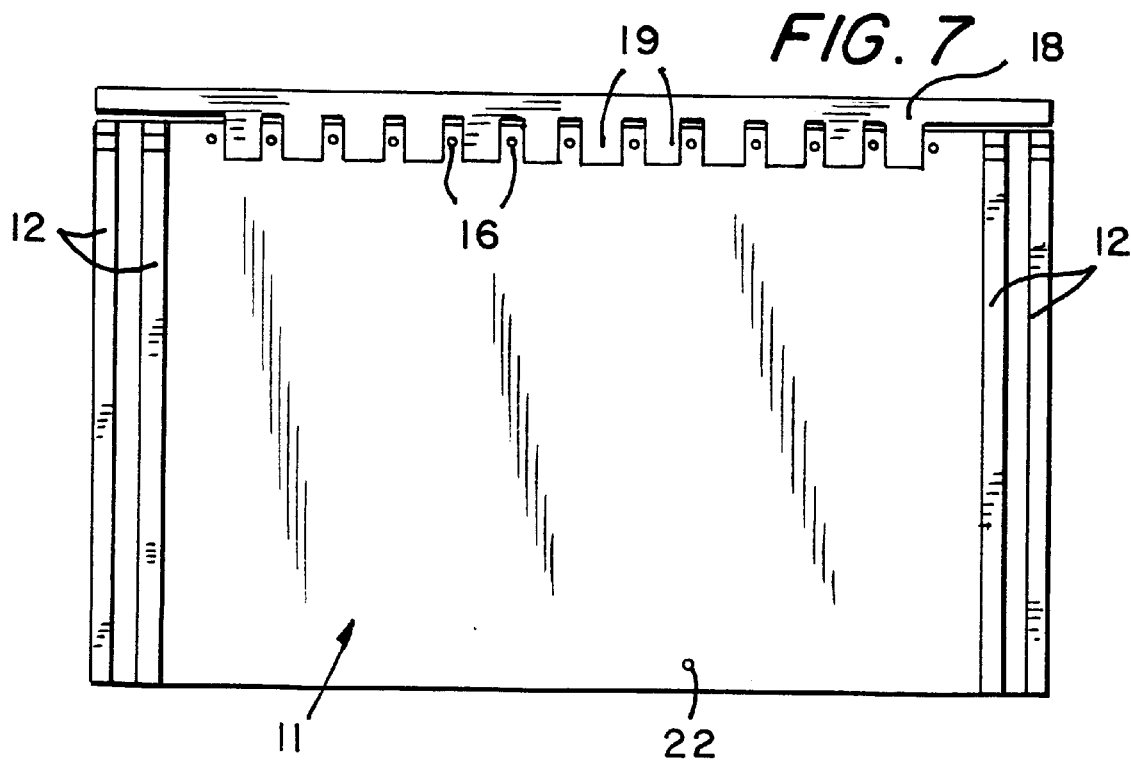

CASSETTE FOR ELECTROPHORETIC GELS

FIELD OF THE INVENTION

The present invention relates to a cassette for use in the formation of an electrophoretic gel and more particularly to such a cassette which includes means to assist ill separating and defining individual sample receiving wells at one end of the electrophoretic gel.

BACKGROUND ART

Electrophoretic gels, usually comprising hydrogels such as agarose or polyacrylamide, are used for the separation of nucleic acids, proteins and other macromolecular compounds. The sample to be separated is placed at one end of the gel and a direct electric field is applied between the ends of the gel causing the components of the sample to migrate through the gel at rates dependent upon their molecular size and charge.

A mixture of components to be separated is normally introduced into one of a number of small wells formed in an upper edge of the gel before the electric current is applied. It is usual to run a number of such mixtures simultaneously on an electrophoretic gel in a side by side arrangement. For this purpose one mixture is placed in each of a series of wells formed in the upper edge of the gel.

It is conventional to form electrophoretic gels by juxtaposing a pair of glass plates in a slightly spaced apart side-by-side relationship and filling the space there between with a liquid which can set and form an electrophoretic gel. The side edges of the space between the glass plates are, in this case, sealed with adhesive tape or a similar material, when the gel is poured a comb is placed in the upper end of the space between the glass plates. After the gel has set the comb can be withdrawn leaving in the top of the gel a series of spaced apart wells, each well having been defined by one tooth of the comb. A tongue of gel remains between the glass plates separating a pair of adjacent wells.

In more recent years it has been proposed to pre-form electrophoretic gels in cassettes formed of synthetic plastics materials. The side walls of the cassette are formed with integral means to connect them together along the sides of the cassette. In U.S. Pat. No. 5,288,465 ribs are provided on the cassette walls to define wells at one end of the cassette. This arrangement has the disadvantage that the walls of the wells interfere with the smooth flow of electric current through the electrophoretic gel.

In the case of pre-formed gels in a cassette, the use of a conventional comb has the disadvantage that upon withdrawal of the comb the tongues of gel may, with time, show an increased tendency to break away from the remainder of the gel. This results in poorly defined wells. Alternatively, if the tongues of gel are left intact upon withdrawal of the comb they may not be firmly adhered to the side wall of the cassette. This means that the tongues may fold over sideways occluding an adjacent well. In either case the smooth and convenient operation of the cassette is inhibited.

The present invention is directed to an alternative arrangement in which the tongues of gel may be maintained in position in the cassette thereby ensuring clear definition of the wells at all times.

DISCLOSURE OF THE INVENTION

In a first aspect, the present invention consists in an improved cassette for use in the formation of an electrophoretic gel comprising two plates with substantially planar walls having two sides and two ends so arranged in a side-by-side, spaced apart array to form a gel receiving space between them, the improvement consisting of a plurality of projections on one or each of the plates, the projections extending into the gel receiving space and the projections being so sized and so spaced apart over the surface of one or each of the plates that when a gel is introduced into the gel receiving space and a well forming comb is inserted into that space, a plurality of spaced wells are formed in the gel, at least some of the wells being separated by a tongue of gel which surrounds and engages at least one of the projections, wherein the projections prevent the tongues of the gel from moving relative to the two plates when the electrophoretic gel is in use.

The projections protrude into the tongue of the gel or go right through the tongue. The projections can be clipped or welded into the opposite wall to improve the rigidity of the cassette, especially when using more flexible plastics.

Each projection is preferably as small as possible in its maximum cross-sectional dimension so that there is minimal disturbance to the flow of electric current through the gel. In the case of one projections per tongue, the projections are preferably each positioned as close to the upper edge of the associated tongue as possible. This allows the current to re-establish parallel flow before meeting samples positioned in the wells. In the case of multiple projections per tongue, the projections can be dispersed throughout the length of the respective tongues.

The projections can also serve to locate and fasten the two plates in a favourable manner. Locating lugs at the side of the cassette can also be used to perform similar locating function.

In a further preferred embodiment of the first aspect of the present invention, a transparent inorganic oxide film is deposited at least upon one surface of the cassette components forming the gel receiving space. It has been found that such films improve the adhesion of the gel to the components of the cassette by mimicking the surface characteristics of glass. Preferably, the transparent inorganic oxide film is formed of silicon, aluminium, zircon or mixtures thereof. It will be appreciated, however, that any other element or elements which will give a transparent oxide film would be suitable. The film can be deposited directly upon the surface by a variety of vacuum coating techniques, many of which are described in Proceedings, Annual Technical Conference—Society of Vacuum Coaters, 1992, published by Society of Vacuum Coaters, Albuquerque, N. Mex., USA. One preferred form of coating suitable for the present invention is Coronal Vacuum Discharge (CVD), Metroline Industries, California. Other appropriate coating methods known to the art or methods for bonding a coated material (Van Lear process) to the surface of the cassette would also be suitable.

It has been disclosed in WO 95/31717 that silicon oxide coating of plastic electrophoresis moulds allows uniform polymerisation of polyacrylamide gels by providing an oxygen impermeable barrier. It will be appreciate that similar coatings would also be applicable for the cassette of the present invention.

The improved electrophoretic gel cassette can further include well identification markings. These can be in the form of numbers or letters locating the positions of the receiving wells or the lanes in which samples are separated during use. Inclusion of markings assists the user to identify samples that have been separated using the cassette. Traditionally, users apply identifying marks on the surface of a plate of the cassette prior to use. These marks can be inadvertently removed during handling of the cassette which can lead to problems of identifying which samples have been separated in which lanes. Having preformed identifying marks on the cassette overcomes this problem.

In a still further preferred embodiment of the present invention, one or more projections are positioned on one or each of the plates and extending into the gel receiving space such that the one or more projections prevent the gel when formed from sliding out of the cassette.

In a second aspect, the present invention consists in an electrophoretic module comprising a cassette according to the first aspect of the present invention containing an electrophoretic gel substantially filling the gel receiving space, tongues of gel extending from one end of the electrophoretic gel in the gel receiving space, each tongue extending to and surrounding at least one of the projections such that there is defined between adjacent tongues sample receiving wells.

In a third aspect, the present invention consists in a process for producing an improved electrophoretic gel comprising, assembling a cassette according to the first aspect of the present invention, casting a gel by introducing an electrophoretic gel mixture into the gel receiving space of the cassette; inserting a well-forming comb between the two plates of the cassette, the comb can be added at any stage of the gel-casting process prior to setting of the gel in the space; and allowing the gel to set.

In order that the present invention may be more clearly understood, a preferred form will be described with reference to the following drawings.

BRIEF DESCRIPTION OF THE DRAWINGS

FIG. 1 is a perspective view of a cassette for an electrophoretic gel according to the present invention;

FIG. 2 is a plan view of the cassette of FIG. 1;

FIG. 3 is a plan view of another embodiment of a cassette according to the present invention;

FIG. 6 is a sectional view along section V—V of one of the walls of the cassette of FIG. 1 when an electrophoretic gel occupies the gel receiving space; and FIG. 7 is an elevation view of the inside face of the walls of the cassette of FIG. 1 when a well forming comb is in place in preparation for the filling of the cassette with an electrophoretic gel forming liquid.

BEST MODE FOR CARRYING OUT THE INVENTION

Figure 4:
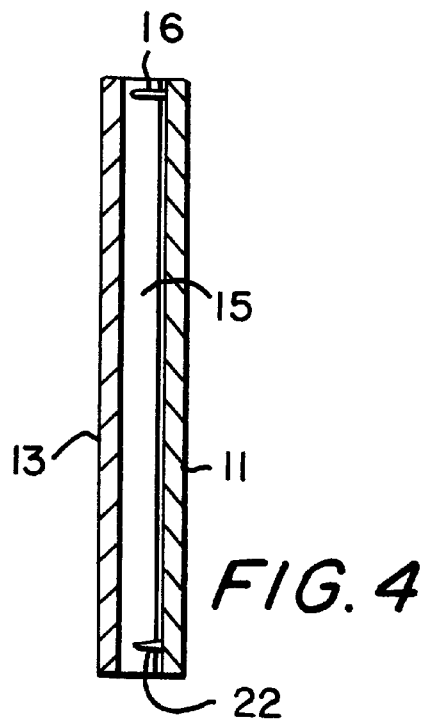
FIG. 4 is a sectional view along section IV—IV through the cassette of FIG. 1.
Figure 5:
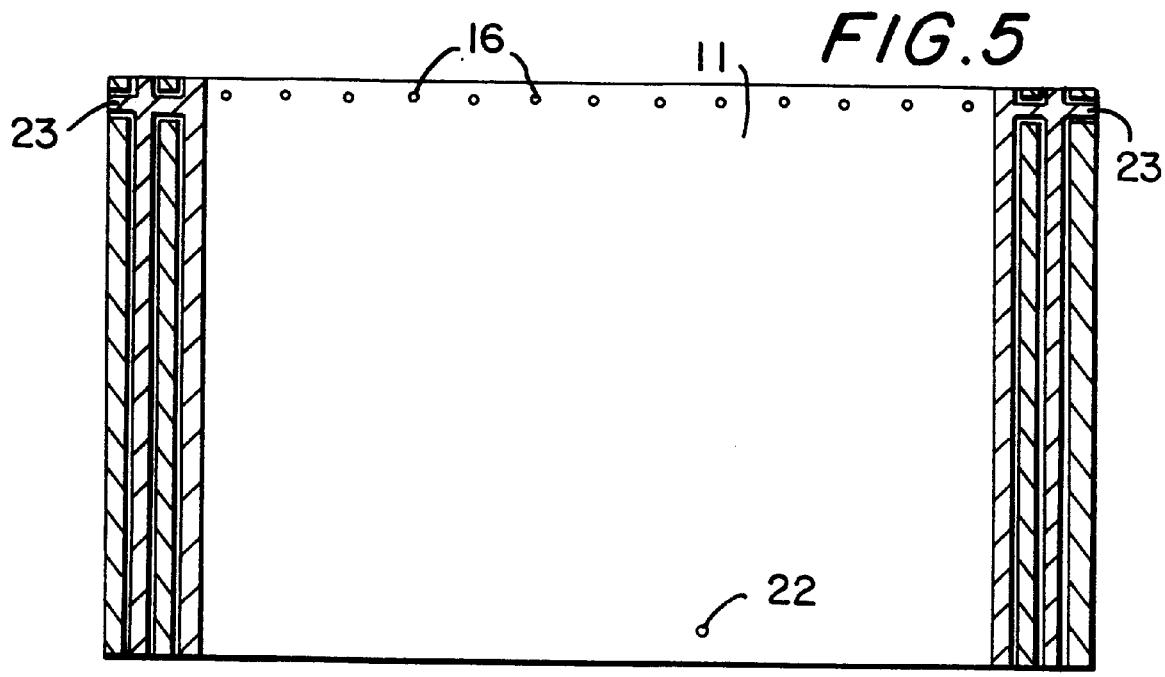
FIG. 5 is a sectional view along section V—V of the cassette of FIG. 1.

The electrophoresis cassette 10 is formed in two parts by injection moulding or by other methods from a suitable synthetic plastics material. One part forms a first side wall 11 of the cassette which is bounded on each side by a connecting means comprising a pair of spaced apart ridges 12. The other part forms a second side wall 13 of the cassette which is bounded on each side by a pair of spaced apart ridges 14. The ridges 12 and 14 interdigitate to form a seal along each side of the cassette 10 to prevent leakage there through of the gel forming liquid during setting of the gel or the electrical current during electrophoresis. The ridges 12 and 14 are of such thickness that a gel receiving space 15 is defined between the side walls 11 and 13 which lie in substantially parallel planes. In order to assist in the positioning of the two parts of the cassette 10, locating lugs 23 are positioned across the ridges 12 and 14. The lugs 23 are positioned relative to or above the bottom of wells 20 formed in the gel so as to ensure that during casting of the gel in the cassette 10, the gel prior to setting does not leak through any space formed by the lugs 23.

The inside surface of the side wall 11 is formed with a plurality of inwardly directed projections 16 which extend into the gel receiving space 15. The projections 16 may originate from either or both of faces 11 and 13 into the gel receiving space 15. Each projection is conical with a base diameter of approximately 0.8 mm and a length which stops just short of completely spanning the gel receiving space 15. Alternatively, (as illustrated in FIG. 3) the projections 16 may extend the whole width of the gel receiving space 15 and extend into corresponding recesses 17 in the opposite cassette. This enables the projections 16 to be used to maintain a consistent space between the two side walls of the cassette (11,13) and, by locking into the other side wall, make the cassette more rigid. In most systems the cassette is clamped into place and therefore this locking can be very important when using less rigid plastics such as PET.

The projections 16 are aligned in a row evenly spaced apart closely adjacent to one end of the side wall 11.

To form a gel in the cassette 10 a comb 18 with a plurality of spaced apart teeth 19 is inserted into one end of the cassette 10. The teeth 19 are so dimensioned that they interdigitate with the projections 16 but are at all times closely spaced therefrom. After the gel has formed in the space 15 the cassette can be used.

When the comb 18 is withdrawn there will be a plurality of wells 20 formed in the gel. The wells 20 are separated by tongues 21 of gel formed when gel forming liquid enters between the adjacent teeth 19 of the comb 18 and sets. Each tongue 21 will extend to and surround one of the projections 16. The projections 16 will serve to support the tongue of gel 21 without substantially disturbing the flow of electric current through the cassette during use.

There can be many projections 16 on each of the side walls 11 and 13 which extend towards one another to partly or fully span the gel forming space 15. Alternatively, projections on the two side walls could alternate across the width of the cassette 10. Rather than being conical the projections 16 could be cylindrical, diamond, or in the form of rectangular or triangular prisms, or other geometrical forms. There may be one or more projections aligned along the length of each tongue. In another embodiment each tongue may surround one or more laterally spaced apart projections.

Optionally, the inside surface of the side wall 11 is formed with at least one inwardly directed projection 22 which extends into the gel receiving space 15. Projections 22 may originate from either or both of faces 11 and 13 into the gel receiving space 15. The projection 22 can be conical, cylindrical, diamond, or in the form of rectangular or triangular prisms, or other geometrical forms. There may be one or more projections 22 aligned along the length of the lower portion of either or both side walls 11 and 13. The projection 22 serves to support the gel when formed while the cassette 10 is in a vertical plane and prevent the gel from slipping out through the bottom of the cassette 10. FIG. 4 shows an embodiment having a conical projection 22 protruding from face 11 into the gel receiving space 15.

In order to assist or improve the adhesion of the gel to the cassette, a transparent inorganic oxide film is deposited at least upon one of the surfaces of the cassette components forming the gel receiving space. It has been found that such films improve the adhesion of the gel to the components of the cassette by mimicking the surface characteristics of glass. The transparent inorganic oxide film is formed of silicon, aluminium, zircon or mixtures thereof. A silicon oxide film is deposited directly upon the inner surface of the walls by using a similar process as disclosed in U.S. Pat. No. 3,442,686.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A cassette for use in the formation of an electrophoretic gel comprising two plates with substantially planar walls each having two sides and two ends so arranged in a side-by-side, spaced apart array to form a gel receiving space between them, the improvement comprising a plurality of projections on one or each of the plates, the projections extending into the gel receiving space and the projections being so sized and so spaced apart over the surface of one or each of the plates that when a gel is introduced into the gel receiving space and a well-forming comb is inserted into the space a plurality of spaced wells are formed in the gel, at least some of the wells being separated by a tongue of gel which surrounds and engages at least one of the projections, wherein the projections prevent the tongues of the gel from moving relative to the two plates when the electrophoretic gel is in use.

2. A cassette as claimed in claim 1 in which the projections protrude through the tongues to the opposite wall.

3. A cassette as claimed in claim 2 in which the projections are clipped or welded into the opposite wall.

4. A cassette as claimed in claim 1 in which each projection causes minimal disturbance to the flow of electric current through the gel in use.

5. A cassette as claimed in claim 1 having one projection per tongue in which the projections are each positioned at or proximal to the upper edge of each associated tongue.

6. A cassette as claimed in claim 1 having multiple projections per tongue in which the projections are dispersed throughout the length of each associated tongue.

7. A cassette as claimed in claim 1 in which a transparent inorganic oxide film is deposited on at least one of the surfaces forming the gel receiving space.

8. A cassette as claimed in claim 7 wherein the transparent inorganic oxide is selected from the group consisting of silicon, aluminium, zircon and mixtures thereof.

9. A cassette as claimed in claim 1 in which the projections also serve to locate and fasten the two plates.

10. A cassette as claimed in claim 1 further including at least one locating lug to locate the two plates when assembled.

11. A cassette as claimed in claim 1 further including identification markings for the wells.

12. A cassette as claimed in claim 1 further including one or more projections positioned on one or each of the plates and extending into the gel receiving space, wherein the one or more projections prevent the gel when formed from sliding out of the cassette.

13. A cassette as claimed in claim 1 in which the gel receiving space contains an electrophoretic gel such that tongues of gel extend from one end of the electrophoretic gel in the gel receiving space, each tongue extending to and surrounding at least one of the projections such that there is defined between adjacent tongues sample receiving wells.

14. A process for producing an improved electrophoretic gel comprising assembling a cassette as claimed in claim 1; casting a gel by introducing an electrophoretic gel mixture into the gel receiving space of the cassette; inserting a well-forming comb between the two plates of the cassette, the comb can be added at any stage of the gel-casting process prior to setting of the gel in the space; and allowing the gel to set.

\* \* \* \* \*